United States Patent
Schuler et al.

(10) Patent No.: US 6,957,106 B2
(45) Date of Patent: *Oct. 18, 2005

(54) IMPLANTABLE METHOD TO REGULATE BLOOD PRESSURE BY MEANS OF CODED NERVE SIGNALS

(75) Inventors: Eleanor Schuler, Rio Rancho, NM (US); Claude K. Lee, Reno, NV (US)

(73) Assignee: Science Medicus, Inc., Albuquerque, NM (US)

( * ) Notice: Subject to any disclaimer, the term of this patent is extended or adjusted under 35 U.S.C. 154(b) by 50 days.

This patent is subject to a terminal disclaimer.

(21) Appl. No.: 10/781,078

(22) Filed: Feb. 18, 2004

(65) Prior Publication Data

US 2004/0236238 A1 Nov. 25, 2004

Related U.S. Application Data

(60) Provisional application No. 60/448,767, filed on Feb. 18, 2003.

(51) Int. Cl.$^7$ .................................................. A61N 1/18
(52) U.S. Cl. .......................................... 607/44; 601/12
(58) Field of Search ................................ 607/2, 44, 62, 607/72–74; 601/12, 153

(56) References Cited

U.S. PATENT DOCUMENTS

| | | | | |
|---|---|---|---|---|
| 5,707,400 A | * | 1/1998 | Terry et al. | 607/44 |
| 6,522,926 B1 | * | 2/2003 | Kieval et al. | 607/44 |
| 6,681,136 B2 | * | 1/2004 | Schuler et al. | 607/44 |

* cited by examiner

*Primary Examiner*—Angela D. Sykes
*Assistant Examiner*—Alyssa M. Alter
(74) *Attorney, Agent, or Firm*—Francis Law Group

(57) ABSTRACT

A method and device for modulating blood pressure. The method comprises selecting waveforms from a storage area that are representative of body organ function. The selected waveforms are then transmitted to a treatment member, which is in direct contact with the body, and which then broadcasts the waveforms to a blood pressure regulatory points within the body to modulate blood pressure. A control module is provided for transmission to the treatment member. The control module contains the waveforms which are selected and transmitted to the treatment member, and computer storage can be provided for greater storage capacity and manipulation of the waveforms.

17 Claims, 2 Drawing Sheets

IMPLANTABLE METHOD TO REGULATE BLOOD PRESSURE BY MEANS OF CODED NERVE SIGNALS

RELATED APPLICATION

This is the non-provisional filing of application Ser. No. 60/448,767, filed on Feb. 18, 2003, entitled "Implantable Method to Regulate Blood Pressure by Means of Coded Nerve Signals."

BACKGROUND OF THE INVENTION

Hundreds of millions of people in the world suffer some type of detrimental blood pressure condition. In the United States it is estimated that 50 million individuals have hypertension (blood pressure over 140/90). Of these 50 million, only about 27% have their blood pressure controlled by a combination of medication, diet and exercise. Up to age 55, more males have hypertension than females. But after age 55, females catch up and about 75% have hypertension. Hypertension is a risk factor for damage to heart, brain, kidney and eyes. The organs concerned with blood pressure are the brain, endocrine glands, blood vessels (arterial & venous) and the heart.

Low blood pressure (hypotension) also occurs and has different consequences for substantial numbers of people. Some people operate their cardiovascular system at lower than normal pressure with little consequences. These people are often cold in their extremities and can be less energetic than they would be if they operated at usual pressure. Nonetheless, for most people an episode of hypotension can be immediately life threatening if not corrected. Hypotension causes general weakness and faintness because of insufficient blood flow to the brain. Posteriorly low blood is aggravated when a person gets out of bed or stands up quickly, causing syncope (fainting). Hence hypotension is a significant risk factor for falls in the elderly. Hypotension can be idiopathic (of unknown cause) or it can be the result of taking excessive amounts of high blood pressure treatment medications. Losing count of medication doses in the elderly often results in taking a second dose unknowingly. The doubling of a medication dose can result in overtreatment of hypertension and cause serious low blood pressure complications.

A number of medications are regularly and routinely used as a treatment method to lower or raise blood pressure. These medications reach endocrine control areas that can dovetail with the actions of the neural control network. Such medications have a well established place in medical treatment but are always a compromise in attaining the results desired and minimizing side effects.

Although blood pressure can be measured with devices directly implanted in the arterial blood stream most studies use noninvasive methods. Such modem methods encircle finger, wrist or arm by automatic devices that provide blood pressure and pulse rate. Usually blood pressure is measured routinely by a device called a sphygmomanometer which consists of a cuff that is wrapped around the arm and inflated. A stethoscope or microphone is utilized to listen to an artery. As the cuff is deflated the first sound of swishing blood is the systolic blood pressure. When deflation continues and sounds disappear, the diastolic blood pressure is provided. The systolic blood pressure is the pressure attained when the heart contracts and pumps blood throughout the body. The diastolic blood pressure measures the resting pressure on the artery walls between heart contractions.

The arteries are large blood vessels in tubular form that transport blood from the heart. Such arteries branch out into smaller blood vessels called arterioles which deliver blood to the tiniest vessels called capillaries. Such capillaries supply all the body's organs with blood containing oxygen and nutrients. The arterial network is muscular in nature with the ability to constrict or relax. Generally, constricted arteries raise blood pressure, and those that are relaxed and dilated, lower blood pressure. The arterioles can be constricted and relaxed by the brain to alter blood pressure and change pulse rate.

Arterial blood pulsates at higher pressure and is oxygen rich which gives it the red coloration. Veins containing oxygen-depleted blood are blue in color, and flow at lower pressure. One can visualize the blue blood coursing through veins on the top-side of the hands and other parts of the body surface. Veins carry blood back to the heart where is pumped back top the lungs to again acquire fresh oxygen prior to again being pumped via the arteries to all parts of the body.

The venous system makes up part of the low-pressure system and serves as a blood reservoir. Veins of the cardiovascular system collect blood from everywhere it has been pumped and then flows it back to the heart. The heart's right atrium then squeezes blood into the right ventricle which then pumps it to the lungs to exchange carbon dioxide for oxygen. The lungs then supply the oxygen enriched blood to the left atrium for loading into the powerful left ventricle which then circulates that blood via arteries, arterioles and capillaries that span the entire body.

The general term, "blood pressure" applies to arterial blood pressure in the circulation system. It fluctuates with each heart beat between a systolic maximum level during contraction and a minimum pressure during its diastolic phase. The geometric mean value is known as the pulse pressure of a human or animal. Blood pressure is usually measured at points on the body where pulses can readily be detected. Monitors for measuring and determining blood pressure come in several familiar forms of sphygmomanometer, all of which can be utilized by both physician and patient. Doctors usually recommend that their blood pressure patients purchase a monitor to use at home as an aid to determining the progress for maintaining proper blood pressure. Blood pressure in the veins is chiefly determined by the blood volume and capacitance of the veins themselves. In the chest (thorax) the large vena cava experiences a pump-like action resulting from respiration mechanical action. In other words the veins are susceptible to a large extent to the pressures against the veins by the surrounding structures. Veins are low-pressure tubular structures which carry blood back to the heart where it is pressurized and sent via the muscular arteries throughout the body. Blood pressure is regulated by neuro-electrical signals that travel from the brain to the heart, kidneys and larger arterial blood vessels. There is also an endocrine participation relating to production of renin and angiotensin enzymes from the kidneys. Some of the neuro-electric signaling is parasympathetic (not controllable by the conscious mind in man or animal. But much of the neuro-electric signaling is sympathetic wherein blood pressure levels are influenced by life events, emergencies, mental worry, agitation or perceived or real-life dangers.

Blood pressure is ever changing in response to body organ demands for oxygen, depending on any given organ's activities. Such oxygen supply must be adequate and not excessive and is supplied by the pumping action of the heart. The rate and tone of heart pumping coupled with the dilation or constriction of blood vessels controls blood pressure. Brain electrical signals coupled with hormone and neurotransmitter chemical action modulate the cardiovascular systems circulatory blood pressure. Some of the neural axons provide neurotransmitter chemicals at their pre-synapses which serves to fine-tune electrical signals as they enter the post-synapse prior to flowing into the heart neuroganglionic plexis and at the blood vessel efferent attachment points. The brain plays a role with its electrical signals for both direct organ control and to signal endocrine organs to produce hormones. These signals can regulate the myocardium (heart muscle) as to the rate of contraction (heart beat) and also control the force of the contraction (pumping action) level to contract softly or smartly so as to propel the blood into the arterial system. At the same time signals to the arterial blood vessel efferent motor neuron attachment points regulate the constriction or dilation of the arteries and thusly have a direct effect on blood pressure. Arterial contraction is also effected by hormones and enzymes from the kidney. Neuro signals to the kidney and the arteries are important players in the blood pressure regulation symphony. Both endocrine and neural signals are in themselves variable so as to modulate responses in answer to overall blood pressure regulatory requirements. This means that there is infinite variability within the collection of available "brain stored programs," for both the hypothalamus (endocrine) and medullopontine (neural switching) to provide efferent signals to fine-tune blood pressure.

The muscular control of arteries is exerted by the brain based on afferent nerve information on the status and need for more or less oxygen by the various body organs. The brain also can constrict any severed ends of an artery to lower blood loss by use of the nerves controlling the muscular structure of the artery itself. Such is an example of how finite neuro-coded brain signals control vascular network activity. Neuron axon synapses can introduce chemical neurotransmitters at their gaps to modulate the traveling electrical signals before they instruct target organs. Such targets in the case of blood pressure regulation would be the heart and the blood vessels.

The peripheral nervous systems consisting of the somatic (body) and autonomic (uncontrollable by a person) systems convey input sensory information to the central nervous system (CNS or brain) via afferent nerves to provide information on body and cardiovascular status. The roll of the CNS is to scan, evaluate by comparing data with stored information, and to process this information prior to responding with efferent neuro-coded impulse signals to modulate performance of the cardiovascular system (heart and blood vessels).

The brain is an organ with information integrating function, organ coordinating and instructional output ability. The spinal cord is an extension of the brain. The upward ascending brain structures include the medulla oblongata and then the pons followed by the mesencephalon (midbrain) and cerebellum before reaching the diencephalon where the hypothalamus and the large cerebral hemispheres are located. The medulla oblongata and then the pons followed by the certain midbrain structures contain sensory information receptors and contain the command neurons from which the coded neuro-motor signals instruct the respective target organs. The first three structures make up the brain stem and are the processing and control centers for blood pressure. The principal actors in blood pressure control are the medullopontine region and the hypothalamus.

It has been established that the electrical action for regulating cardiovascular blood pressure emerges from the medullopontine area via the vagus nerve bundle. The vagus nerve bundle contains both afferent and efferent nerves that travel long distances to numerous organs. The medullopontine area is keenly interactive with the body it lives in, to insure that the basic life functions are operating and keeping with their original purpose. All organs, including the brain, require continuous oxygen transport by the blood stream to occur at sufficient speed and volume to do the job. Therefore, the brain gives high priority to adjusting cardiovascular performance so as not to injure any body organ because of insufficient or untimely oxygen. The brain itself is more sensitive than all the organs to hypoxia. Hypoxia is inadequate availability of oxygen from the blood stream. Brain cells begin to die in a few minutes, and in 10 minutes without oxygen, death is certain.

The brain's electrical signals are encoded via specific coded nerve signals but such electrical signals are modified at synaptic gaps located at the junction of the nerve axon and the effector organ. All of this modification is a fine-tuning process that is even influenced by end organ local events. Endocrine gland secretions and neurotransmitter chemicals available at the synaptic gaps can and do alter the received brain signal to meet the demands of what is happening even outside the body as a result of information from the eyes skin or ears. Feedback from numerous afferent sensors provide information and action from the endocrine system to modulate the efferent signals at or prior to arrival at the organs regulated. Actual instructions (brain signals) to any particular target organ almost always require modulation because of life continuum demands with their ever changing performance and environmental pressures.

Blood vessels are muscles which are constricted or dilated to provide correct blood circulation performance. As part of this performance, control of the heart is also modulated as to beat rate and myocardial contractile tone. Information sent to the brain regarding performance status is provided by afferent sensors that are situated in the arteries and span the body. Such afferent sensors can be chemical, mechanical, thermal and pressure receptors that provide minute low voltage informational signals to the brain. For example mechanical sensors can provide information on how much distension is occurring in the artery wall and oxygen sensors can provide information on blood oxygen content. Such signals can be from outside the body as provided by auditory or visual afferent sensors or internal sensors located within the cardiovascular system and elsewhere. Computations made within the medullopontine region of the brain develop "most probable" output efferent signal instructions after considering afferent sensors information. This goes on as a continuous cardiovascular modulation process throughout life. In addition to the electrical signals which have direct effect on the muscles of the heart arteries there are chemicals produced to modulate blood pressure. An example of response to acute-low-blood pressure is to electrically stimulate release of renin in kidney arteries. The renin chemical release happens because of a baroreceptor detecting low blood pressure. Also angiotensin II, the most potent vasoconstrictor is released and acts directly on the arterioles to raise blood pressure.

As the heart contracts and pumps blood (systole), the arteries stretch and store potential energy. When the heart relaxes (diastole) the arteries rebound and keep the blood flowing. This is called the "windkessel" effect and assures continuing circulation to supply of oxygen and nutrients to all parts of the body between heartbeats (contractions).

Regulation of the cardiovascular circulatory system ensures that the entire body is provided with enough blood, not only when at rest but also in situations of extreme exertion or danger. This system can redistribute blood flow to critical organs or deny it to organs that can get by on less flow for a while. For example, digestion causes larger blood volume to the gastrointestinal system. But if an emergency occurs digestion is put on hold and the blood is redirected to the brain or muscles. When the emergency is over the blood flow is returned to the task of digestion.

Regulation of blood flow to the various organs is mainly achieved by alterations in the diameter of the blood vessel lumen (inside bore). The lumen can be incrementally constricted or dilated as required. This lumenal control is accomplished by chemical effects and neural instructions coming from the brain. Blood vessels consist of smooth muscle and contain electrically active cells that continually vary between constriction and relaxation. Nervous control of the blood vessels is mediated with only a few exceptions by the sympathetic nerves of the autonomic nervous system. Parasympatetic nerve division effects on blood pressure, including the participation of the heart are regulated without conscious participation of the individual. The diencephalon, including the thalamus is an important switch point for the various sensory inputs from eyes, ears and skin as well as other parts of the brain. The diencephalon also houses the hypothalamus which plays an important role in the integration of the nervous system and the endocrine system. Modern oral and injectable medications that improve blood pressure, function largely through endocrine aspects. Neurological performance factors (and tolerates) the presence of cardiovascular medications to balance blood pressure. Evidently, good and bad changes inflicted upon blood pressure by medications seem to work along with the brainstem command motor neurons who keep doing their job the best they can.

Central control of the circulation system is effected by the medullopontine region of the brain. This is a critical part of the brain because its span of control stretches across not only the cardiovascular system, but also the respiratory, digestive and other homeostasis functions. The medullopontine region is located at the top of the spinal column and consists of the medulla oblongata and the immediately superior pons structure. These particular structures make few mistakes unless there is hemorrhage, physical damage or malignancy that crosses critical pathways. Most of the life support control of the human or animal body is via the vagus (or tenth cranial) nerve that exits from the medulla oblongata. This nerve is actually a long bundle of afferent and efferent neurons that travels over the internal body to most organs. The vagus nerve emerges from each side of the medulla and travels different routes to the same target organs. Paralysis or severing the two vagus nerves at the level of the medulla or neck is rapidly fatal. Severing a single vagus nerve at the level of the neck will impair life processes and the physicians attending would certainly have their hands full in sustaining life, but it is possible. Other cranial and peripheral nerve routing is found throughout the body and the spinal cord that regulate the cardiovascular system, including the regulation of blood and the spinal cord that regulate the cardiovascular system, including the regulation of blood pressure in a symphony of life equilibrium (body homeostasis).

In the arterial high pressure control side there are stretch and pressure receptor afferent nerves from the aorta and carotid arteries to provide key information. In the low pressure venous system stretch and other receptors located in the vena cava, atrial heart chambers and in the left ventricle provide blood pressure pulse rate and filling pressure data to the brains medullopontine. Afferent sensory data which compute into efferent nerve signals back to the cardiovascular system is processed in various nucleus tracts of the medulla oblongata and its olive. Alterations in newly arriving afferent data is compared to existing efferent control output before modulative corrective responses are elicited and sent off to the heart and blood vessels.

An important part of blood pressure regulation requires the participation of the adrenal gland medulla for its production of hormonal chemical signals for the control of blood pressure. The adrenal medulla is a neuro-endocrine transducer wherein electrical impulses from the sympathetic preganglion nerve fibers are transformed into hormonal signals. The principal hormones produced in response to the electrical signals are epinephrine or adrenaline, norepinephrine and noradrenaline. Such hormones are released into the blood stream and are collectively called catecholamines. The hypothalamus is the principal brain center that electrically regulates the adrenal response to mental or physical stress. The adrenal glands sit atop the kidney.

The adrenal medulla usually functions at a low level of activity except in situations of physical or psychic stress, where larger quantities of catecholamines are released. Such catecholamines play a part in the postganglionic synaptic nerve endings as well as some synaptic gaps in the brain, especially the hypothalamus. Generally, once the adrenal medulla is turned on electrically to produce hormones in response to stress they circulate for some considerable time (up to about 4 hours) and are a principal cause for elevating blood pressure.

The hypothalamus, located in the brain, has considerable effect on the endocrine system and is intimately connected with the pituitary gland which can secrete hormones into a blood portal for fast entry into the blood stream. Electrical afferent signals play a significant role in setting off the hormone releases in the endocrine system. When the afferent nerves signal the hypothalamus that the mental or physical stress is reduced then stimulation of catecholamines reduces and returns to normal function. Therefore, it is possible to broadcast countermanding signals to afferent nerves to change blood pressure by tricking the autonomic regulating factors.

SUMMARY OF THE INVENTION

The invention provides a method for modulating blood pressure. Stored waveforms representative of waveforms that are generated and carried in the body are selected from a storage area. The selected waveforms are then transmitted to a treatment member which is in direct contact with the body. The treatment member then broadcasts the selected waveforms to an organ in the body.

The waveforms may be selected from a storage area in a computer, such as a scientific computer. The process of transmitting the selected waveforms can either be done remotely or with the treatment member connected to a control module. The transmission may be seismic, electronic, or via any other suitable method.

The invention further provides an apparatus for modulating blood pressure. The apparatus includes a source of collected waveforms that are indicative of body organ functioning, a treatment member formed to be in direct contact with the body, means for transmitting collected waveforms to the treatment member, and means for broadcasting the collected waveforms from the treatment member to a body organ.

The transmitting means may include a digital to analog converter. The source of collected waveforms preferably comprises a computer which has the collected waveforms stored in digital format. The computer may include separate storage areas for collected waveforms of different categories.

The treatment member may be comprised of an antenna or an electrode, or any other means of broadcasting one or more waveforms directly to the body.

BRIEF DESCRIPTION OF THE DRAWINGS

The invention is described in greater detail in the following description of examples embodying the best mode of the invention, taken in conjunction with the drawing figures, in which.

DESCRIPTION OF EXAMPLES EMBODYING THE BEST MODE OF THE INVENTION

Figure 1:
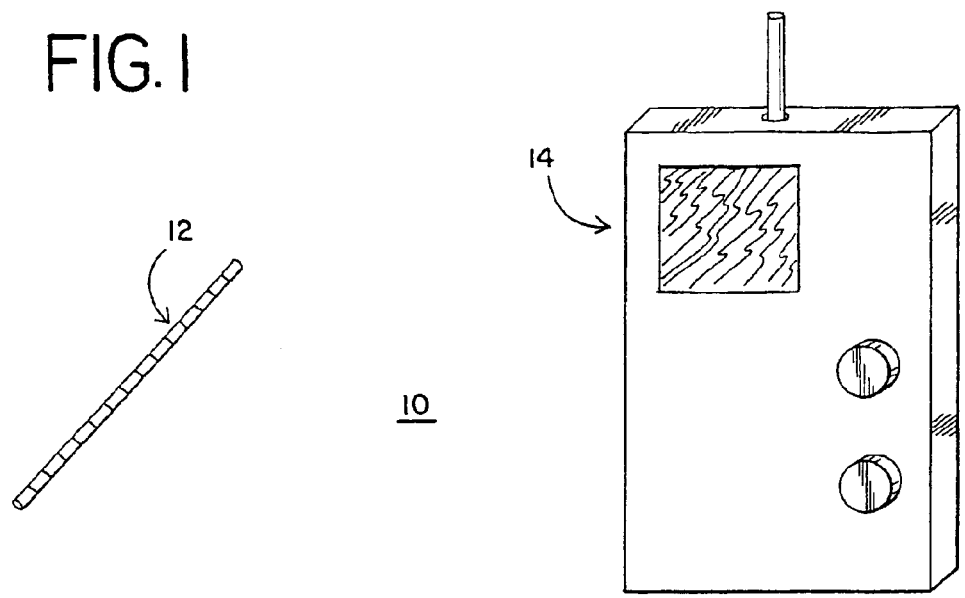
FIG. 1 is a schematic diagram of one form of apparatus for practicing the method according to the invention.

For the purpose of promoting an understanding of the principles of the invention, references will be made to the embodiments illustrated in the drawings. It will, nevertheless, be understood that no limitation of the scope of the invention is thereby intended, such alterations and further modifications in the illustrated device, and such further applications of the principles of the invention illustrated herein being contemplated as would normally occur to the one skilled in the art to which the invention relates.

There is need to provide a fast electrical method to regulate blood pressure. Additionally, there is need for an implantable electrical device to regulate long-term blood pressure, just as an implantable heart pacemaker similarly serves the patient for many years. The invention consists of an electrical method to modulate signals going to the brain (via afferent sensory nerves) and nerves coming from the brain (via efferent nerves). Some of the electrical signals are transmitted with antenna or connections to modulate efferent signals to the heart and blood vessels coming from the medullopontine brainstem region. Other signals are sent to the hypothalamus to influence hormonal effects on blood pressure. This invention has use in the emergency rooms to treat sever hypertension or hypotension. As an implantable device this invention offers a treatment to selected patients who have no alternative for modulation of their blood pressure.

The invention disclosed herein consists of a waveform receiver and generator to process neural signals to elucidate (make lucid or clear) present status and then to transmit new instructions to alter blood pressure values for the benefit of the patient. The invention has the capability to modulate both endocrine and neural inputs that are involved in blood pressure regulation. The invention is meant to work in concert with present medications initially but the invention may allow for resetting base blood pressure levels to such an extent that previously prescribed medications may be reduced or eliminated as a treatment modality.

The invention encompasses both a device and method for modulating blood pressure by electrical waveforms. One form of a device 10 used for modulating blood pressure by electrical waveforms, as shown in FIG. 1, is comprised of at least one treatment member 12, and a control module 14. The device used in this invention is described in greater detail in U.S. Pat. No. 6,681,136, issued Jan. 20, 2003, and entitled "Method to Modulate Blood Pressure By Electrical Waveforms," the disclosure of which is incorporated herein by reference.

Figure 2:
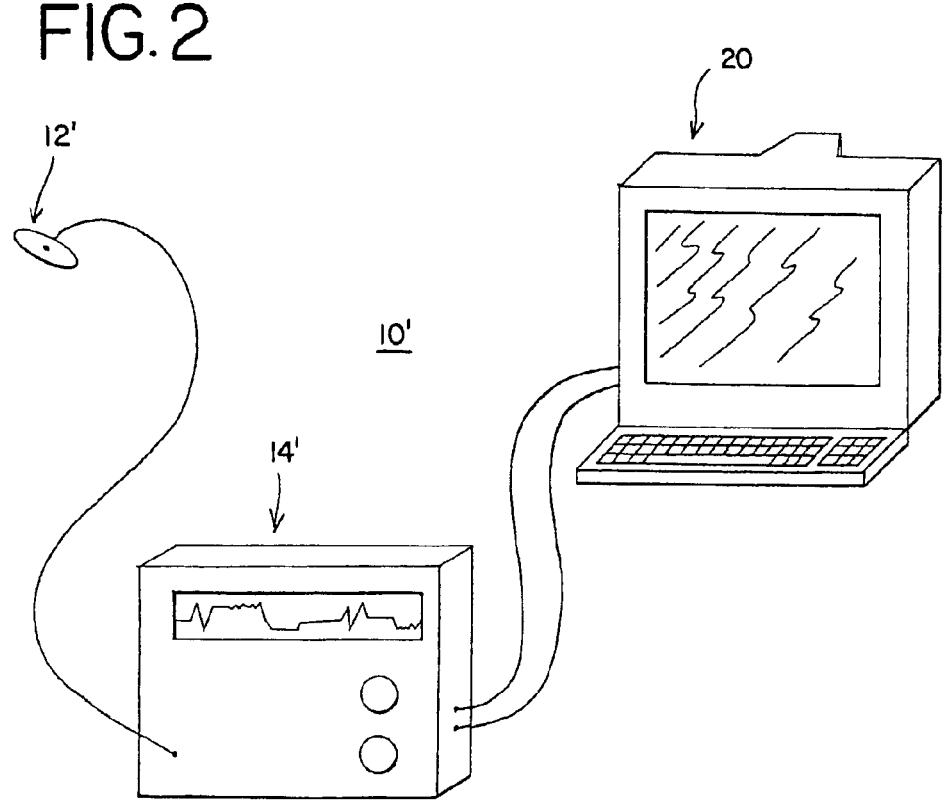
FIG. 2 is a schematic diagram of another form of apparatus for practicing the method according to the invention.

In an alternate embodiment of the device 10, as shown in FIG. 2 and as described in greater detail in the above patent application incorporated herein by reference, a control module 14' and treatment member 12' are connected. Similar members retain the same reference numerals in this figure. Additionally, FIG. 2 further shows another embodiment of the device 10' as being connected to a computer 20, which provides greater capacity to store the waveform signals. The computer 20 is used to store the unique waveform signals which are complex and unique to each organ and function of the organ.

Figure 3:
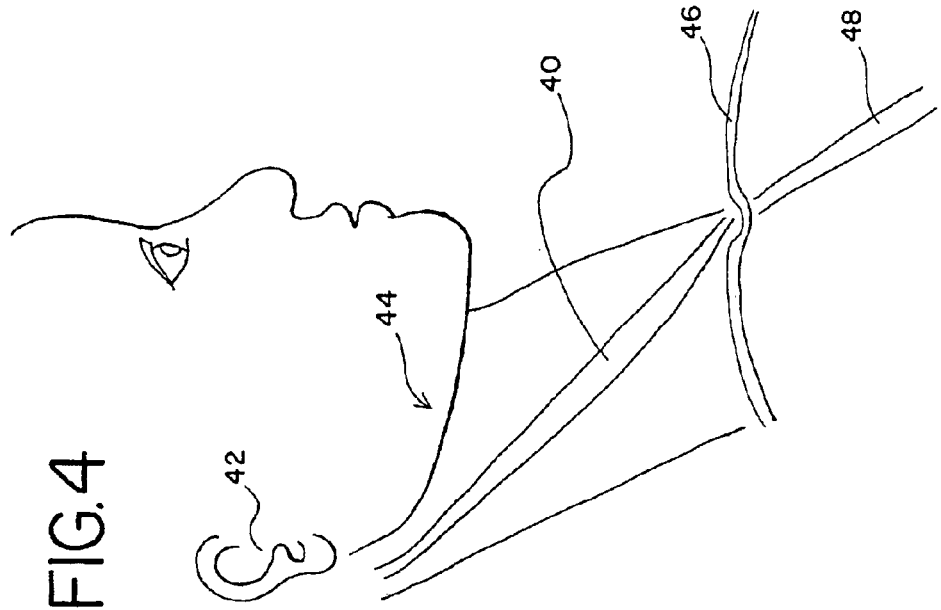
FIG. 3 is a flow chart of the method according to the invention.
Figure 4:
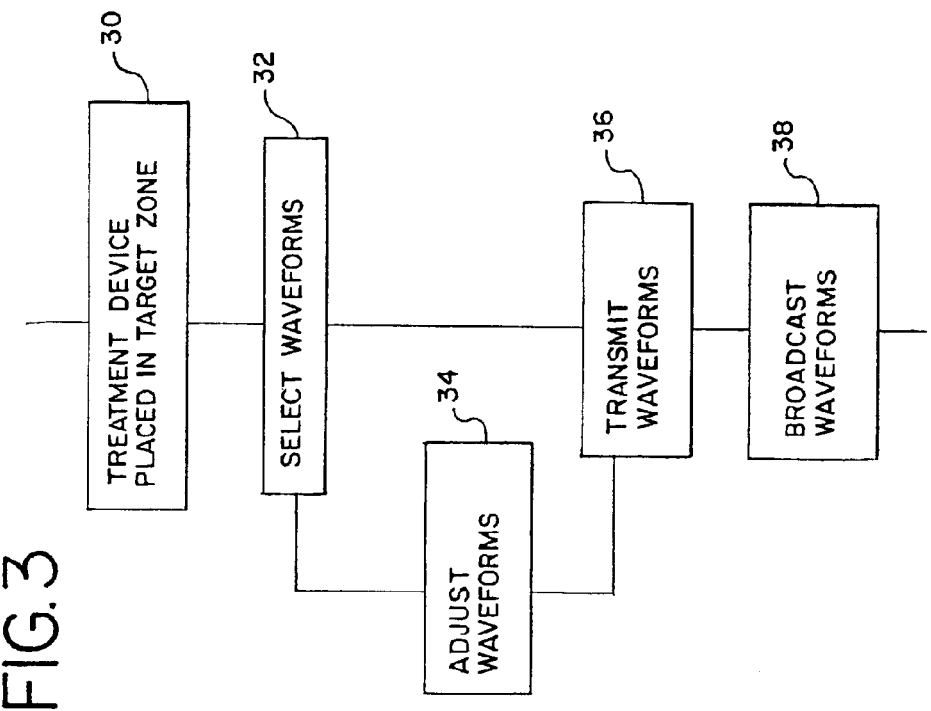
FIG. 4 is a schematic diagram of one of the blood pressure regulatory points treated by the invention.

The invention further includes a method, as shown in FIG. 3, for using the device 10, 10' to modulate blood pressure by electrical waveforms. The method begins at step 30 by placing the treatment member 12, 12' on a blood pressure regulatory point 40, as shown in FIG. 4, which includes the area around the carotid body and carotid sinus between the angle of the jaw 44 at the ear 42 down to the clavicular notch, which is where the clavicular bone 46 meets the sternum 48. Alternatively, the blood pressure regulatory point 40 can include appropriate afferent or efferent nerves connected to the aortic arch. Once the treatment member 12, 12' is placed on the target zone 40, at step 32 one or more stored electrical waveform signals are selected from a menu of catalogued waveform signals.

The waveform signals, and their creation, are described in greater detail in U.S. Pat. application Ser. No. 10/000,005, filed on Nov. 20, 2001, and entitled "Device and Method to Record, Store, and Broadcast Specific Brain Waveforms to Modulate Body Organ Functioning," the disclosure of which is incorporated herein by reference. Such application contains representative types of waveforms that are also operative in the control of human or animal blood pressure. Such waveforms or any combination of segments of the waveforms presented in the above mentioned provisional patent application are representative of the kinds of signals operating with neuron circuits emanating from the medullopontine region of the brain. Such waveforms can be used to modulate either afferent or efferent nerves that play a part in control or fine-tuning of blood pressure. Such waveform signals are similar to those naturally produced by the brain stem structures for modulating blood pressure, as described in greater detail in the immediately above-identified incorporated application.

Once selected, the waveform signals may be adjusted, step 34, to perform a particular function with respect to modulating blood pressure in the body. The actual adjustment forms no part of the present invention. Alternatively, if it is decided that the waveform signals do not need to be adjusted, step 34 is skipped and the process proceeds directly to step 36. At step 36, the waveform signal is transmitted to the treatment member 12, 12' of the device 10, 10'.

Upon receipt of the waveform signals, the treatment member 12, 12' in step 38 broadcasts the waveform signals to the target zone 40. The treatment member 12, 12' may be conventional, or may be specially developed just to transmit the unique waveform signals. The device 10, 10' utilizes appropriate waveform signals to modulate blood pressure via conduction or broadcast of electrical signals into the target zone 40.

In one embodiment of the invention, the process of broadcasting by the treatment member 12, 12' is accomplished by direct conduction or transmission through unbroken skin to the target zone 40. The target zone 40 will approximate a position close to the nerve or nerve plexus onto which the signal is to be imposed. The treatment member 12, 12' is brought into contact with the skin in the target zone 40 that allows for the transport of the signal to the target nerve.

In an alternate embodiment of the invention, the process of broadcasting the waveform is accomplished by direct conduction via attachment of an electrode to the receiving nerve or nerve plexus. This requires a surgical intervention as required to physically attach the electrode to the selected target nerve.

In yet another embodiment of the invention, the process of broadcasting is accomplished by transposing the waveform into a seismic form where it is sent into the target zone 40 in a manner that allows the appropriate "nerve" to receive and to obey the coded instructions of such seismic signal. The treatment member 12, 12' is pressed against the unbroken skin surface using an electrode conductive gel or paste medium to aid conductivity.

Various features of the invention have been particularly shown and described in connection with the illustrated embodiments of the invention. However, it must be understood that these particular products, and their method of manufacture, do not limit but merely illustrate, and that the invention is to be given its fullest interpretation within the terms of the appended claims.

We claim:

1. A method for modulating blood pressure in a body, comprising the steps of:
    providing a treatment member, said treatment member being adapted to be in communication with the body;
    providing a plurality of waveform signals representative of waveform signals generated in the body and carried by neurons in the body, said plurality of waveform signals including first waveform signals operative in the control of blood pressure, said plurality of waveform signals being stored in a storage medium;
    selecting from said storage medium said first waveform signals;
    transmitting said first waveform to said treatment member; and
    broadcasting said first waveform signals from said treatment member directly to a blood pressure regulatory point in the body.

2. The method of claim 1, wherein said storage medium comprises a memory region in a computer.

3. The method of claim 1, wherein said step of transmitting said first waveform signals comprises remotely transmitting said first waveform signals to said treatment member.

4. The method of claim 1, wherein said step of transmitting said first waveform signals comprises seismic transmission of said first waveform signals to said treatment member.

5. The method of claim 1, wherein said treatment member is adapted to be implanted within the body.

6. An apparatus for modulating blood pressure in a body, comprising:
    a source of collected waveform signals indicative of body organ functioning, said waveform signals including first waveform signals operative in the control of blood pressure;
    a treatment member adapted to be in communication with the body, said treatment member being further adapted to broadcast said first waveform signals directly to a blood pressure regulatory point in the body; and
    a transmission apparatus adapted to transmit said first waveform signals to said treatment member.

7. The apparatus of claim 6, wherein said transmission apparatus includes a digital to analog converter.

8. The apparatus of claim 6, wherein said source comprises a computer having said collected waveform signals stored in digital format.

9. The apparatus of claim 8, wherein said computer includes separate storage areas for collecting waveform signals of different blood pressure functional categories.

10. The apparatus of claim 6, wherein said treatment member includes an antenna for broadcasting said first waveform signals.

11. The apparatus of claim 6, wherein said treatment member comprises an electrode.

12. The method of claim 6, wherein said treatment member is adapted to be implanted within the body.

13. The method of claim 1, wherein said treatment member is adapted to be in contact with the body.

14. The apparatus of claim 6, wherein said treatment member is adapted to be in contact with the body.

15. A method for modulating blood pressure in a body, comprising the steps of:
    providing a treatment member, said treatment member being adapted to be implanted in the body;
    providing a plurality of waveform signals representative of waveform signals generated in the body and carried by neurons in the body, said plurality of waveform signals including first waveform signals operative in the control of blood pressure;
    transmitting said first waveform to said treatment member; and
    broadcasting said first waveform signals from said treatment member directly to a blood pressure regulatory point in the body, whereby the blood pressure is modulated.

16. The method of claim 15, wherein said blood pressure regulatory point comprises a point selected from the group consisting of the vagus nerve, hypothalamus region of the brainstem, medulla region of the brainstem and medullopontine region of the brainstem.

17. An apparatus for modulating blood pressure in a body, comprising:
    a source of collected waveform signals indicative of body organ functioning, said waveform signals including first waveform signals operative in the control of blood pressure;
    a treatment member adapted to be implanted in the body, said treatment member being further adapted to broadcast said first waveform signals directly to a blood pressure regulatory point in the body; and
    a transmission apparatus adapted to transmit said first waveform signals to said treatment member.

* * * * *